(12) United States Patent
Gleicher et al.

(10) Patent No.: US 7,615,544 B2
(45) Date of Patent: *Nov. 10, 2009

(54) METHOD OF IMPROVING CUMULATIVE EMBRYO SCORE AND QUANTITY OF FERTILIZED OOCYTES, INCREASING EUPLOIDY RATE AND OF NORMALIZING OVARIAN FUNCTION USING AN ANDROGEN SUCH AS DEHYDROEPIANDROSTERONE

(75) Inventors: Norbert Gleicher, Chicago, IL (US); David H. Barad, Closter, NJ (US); Dwyn V. Harben, Bryn Mawr, PA (US)

(73) Assignee: American Infertility of New York, New York, NY (US)

( * ) Notice: Subject to any disclaimer, the term of this patent is extended or adjusted under 35 U.S.C. 154(b) by 26 days.

This patent is subject to a terminal disclaimer.

(21) Appl. No.: 11/269,310

(22) Filed: Nov. 8, 2005

(65) Prior Publication Data

US 2006/0089339 A1 Apr. 27, 2006

Related U.S. Application Data

(63) Continuation-in-part of application No. 10/973,192, filed on Oct. 26, 2004, now abandoned.

(51) Int. Cl.
*A61K 31/56* (2006.01)
(52) U.S. Cl. .................................... 514/169; 514/177
(58) Field of Classification Search ................. 514/169, 514/177; 800/21
See application file for complete search history.

(56) References Cited

U.S. PATENT DOCUMENTS

| | | | |
|---|---|---|---|
| 4,670,401 | A | 6/1987 | Cutler et al. |
| 4,931,403 | A | 6/1990 | Cutler et al. |
| 6,352,997 | B1 | 3/2002 | Waldsteicher et al. |
| 6,548,087 | B1 | 4/2003 | Kent et al. |

OTHER PUBLICATIONS

Visser et al. Human Reproduction, 1993, 8, 1719-1722.*
Lutz et al. PNAS, 2001, 98, 13728-13733.*
Hammes S. R. Molecular Endocrinology, 2004, 18(4) 769-775 (minireview).*
Genazzani et al. Fertility and Sterility, 2001, 76, 241-248.*
Morales et al. Journal of Clinical Endocrinology and Metabolism, 1994, 78, 1360-1367.*
Damario et al. Human Reproduction, 1997, 12, 2359-2365.*
Barad et al. Fetility and Sterility, 2005, 84, 756.e1-756.e3.*
Muasher S. J. Journal of Assisted reproduction and Genetics, 1993, 10, 112-114.*
Lewin et al. Journal of Assisted Reproduction and Genetics, 1994, 11, 500-503.*
Fasouliotis et al. Journal of Assisted Reproduction and Genetics, 2000, 17, 357-373 (review).*
Barad et al. Fertility and Sterility, 2005, 84, Suppl. 1, S42 (Abstract).*
Hugues J. N. Current Practices and Controversies in Assisted reproduction: Meeting report "Medical, Ethical and Social Aspects of Assisted Reproduction", World Health Organization, Sep. 17-21, 2001, p. 102-125.*
Weering et al. Human Reproduction, 2001, 16, 1537-1538 (Letters to the Editor).*
Anderson et al. The Anatomical record, 1997, 249, 44-53.*
Barad et al. (Fertility and Sterility, Sep. 2005, 84, Supplement 1, p. S42: Abstract).*
Casson et al. (Human Reproduction, 2000, 15, 2129-2132).*
Genazzani et al. (Fertility and Sterility, 2001, 76, 241-248).*
MedicineNet.com (Definition of Cells, reproductive, retrieved on Apr. 3, 2008 via http://www.medterms.com).*
Casson et al. (Human Reproduction, 2000, vol. 15, p. 2129-2132).*
Visser et al. (Human Reproduction, 1993, vol. 8, p. 1721, Discussion section).*
Aging and infertility in women: a committee opinion. Fertil Steril 2002;78(1):215-9.
Navot D, Bergh PA, Williams MA, et al. Poor oocyte quality rather than implantation failure as a cause of age-related decline in female fertility. Lancet 1991;337(8754):1375-7.

(Continued)

*Primary Examiner*—Sreeni Padmanabhan
*Assistant Examiner*—Mei-Ping Chui
(74) *Attorney, Agent, or Firm*—Beem Patent Law Firm

(57) ABSTRACT

A method of improving cumulative embryo score may comprise administering an androgen to a human female, for example, DHEA, for at least about four consecutive months followed by harvesting and fertilizing oocytes and forming embryos. Between about 50 mg and about 100 mg of DHEA may be administered to a human female per day. Moreover, a method of increasing the quantity of fertilized oocytes in one cycle of in vitro fertilization may comprise administering an androgen to a human female for at least about four consecutive months, harvesting and fertilizing the oocytes. Furthermore, a method of increasing the quantity of day 3 embryos from one cycle of in vitro fertilization may comprise administering an androgen for at least about four consecutive months, harvesting and fertilizing the oocytes and forming day 3 embryos. A method of normalizing ovarian DHEA also may include administering an androgen for at least about four consecutive months. A method of increasing the euploidy rate in embryos may include administering an androgen for at least about four consecutive weeks.

4 Claims, 4 Drawing Sheets

OTHER PUBLICATIONS

Scott RT, Leonardi MR, Hofmann GE, Illions EH, Neal GS, Navot D. A prospective evaluation of clomiphene citrate challenge test screening of the general Infertility population. Obstet Gynecol 1993;82(4 Pt 1):539-44.

Scott RT, Jr. Evaluation and treatment of low responders. Semin Reprod Endocrinol 1996;14(4):317-37.

Scott RT, Jr., Hofmann GE. Prognostic assessment of ovarian reserve. Fertil Steril 1995;63(1):1-11.

Chuang CC, Chen CD, Chao KH, Chen SU, Ho HN, Yang YS. Age is a better predictor of pregnancy potential than basal follicle-stimulating hormone levels in women undergoing in vitro fertilization. Fertil Steril 2003;79(1):63-8.

Orvieto R, Bar-Hava I, Yoeli R, et al. Results of in vitro fertilization cycles in women aged 43-45 years. Gynecol Endocrinol 2004;18(2):75-8.

Zlebe S, Loft A, Petersen JH, et al. Embryo quality and developmental potential is compromised by age. Acta Obstet Gynecol Scand 2001;80(2):169-74.

Terriou P, Sapin C, Giorgetti C, Hans E, Spach JL, Rouller R. Embryo score is a better predictor of pregnancy than the number of transferred embryos or female age. Fertil Steril 2001;75(3):525-31.

Karande V, Morris R, Rinehart J, Miller C, Rao R, Gleicher N. Limited success using the "flare" protocol in poor responders in cycles with low basal follicle-stimulating hormone levels during in vitro fertilization. Fertil Steril 1997;67(5):900-3.

Schoolcraft W, Schlenker T, Gee M, Stevens J, Wagley L. Improved controlled ovarian hyperstimulation in poor responder in vitro fertilization patients with a microdose follicle-stimulating hormone flare, growth hormone protocol. Fertil Steril 1997;67(1):93-7.

Surrey ES, Bower J, Hill DM, Ramsey J, Surrey MW. Clinical and endocrine effects of a microdose GnRH agonist flare regimen administered to poor responders who are undergoing in vitro fertilization. Fertil Steril 1998;69(3):419-24.

Toner JP, Flood JT. Fertility after the age of 40. Obstet Gynecol Clin North Am 1993;20(2):261-72.

Barad D GN. Increased Oocyte Production after Treatment with Dehydroepiandrosterone. Ferility and Sterility 2005;(in press).

Steer CV, Mills CL, Tan SL, Campbell S, Edwards RG. The cumulative embryo score: a predictive embryo scoring technique to select the optimal number of embryos to transfer in an in-vitro fertilization and embryo transferprogramme Hum Reprod 1992;7(1):117-9.

Van Wagenen G, Simpson M. Embryology of the ovary and testis, *Homo sapiens* and *Macaca mulatta*. New Haven: Yale University Press; 1965.

Block E. A quantitative morphological investigations of the follicular system in newborn female infants. Acta Anat (Basel) 1953;17:201-6.

Forabosco A, Sforza C, De Pol A, Vizzotto L, Marzona L, Ferrario VF. Morphometric study of the human neonatal ovary. Anat Rec 1991;231(2):201-8.

Gougeon A. Dynamics of follicular growth in the human: a model from preliminary results. Hum Reprod 1986;1(2):81-7.

Richards JS, Russell DL, Robker RL, Dajee M, Alliston TN. Molecular mechanisms of ovulation and luteinization. Mol Cell Endocrinol 1998;145(1-2):47-54.

McGee EA, Hsueh AJW. Initial and Cyclic Recruitment of Ovarian Follicles. Endocr Rev 2000;21(2):200-14.

Hsueh AJ, Billig H, Tsafriri A. Ovarian follicle atresia: a hormonally controlled apoptotic process. Endocr Rev 1994;15(6):707-24.

Kaipia AJ, Hsueh AJ. Regulation of ovarian follicle atresia. Annu Rev Physiol 1997;59:349-63.

Robker RL, Richards JS. Hormonal Control of the Cell Cycle in Ovarian Cells: Proliferation Versus Differentiation. Biol Reprod 1998;59(3):476-82.

Harlow C, Shaw H, Hillier S, Hodges J. Factors influencing follicle-stimulating hormone—responsive steroidogenesis in marmoset granulosa cells: Effects of androgens and the stage of follicular maturity. Endocrinology 1988;122:2780-7.

Dorrington JH, Moon YS, Armstrong DT. Estradiol 17[beta] biosynthesis in cultured granulosa cells from hypophysectomized immature rats; stimulation by follicle stimulating hormone. Endocrinology 1975;97(5):1328-31.

Hillier SG, Whitelaw PF, Smyth CD. Follicular oestrogen synthesis: The 'two-cell, two-gonadotrophin' model revisited. Molecular and Cellular Endocrinology 1994;100(1-2):51-4.

Bonser J, Walker J, Purohit A, et al. Human granulosa cells are a site of sulphatase activity and are able to utilize dehydroepiandrosterone sulphate as a precursor for oestradiol production. J Endocrinol 2000:167(3):465-71.

Haning R. Jr, Hackett R, Flood C, Loughlin J, Zhao Q, Longcope C. Plasma dehydroepiandrosterone sulfate serves as a prehormone for 48% of follicular fluid testosterone during treatment with menotropins. J Clin Endocrinol Metab 1993;76(5):1301-7.

Hillier SG. Sex steroid metabolism and follicular development in the ovary. Oxford Reviews Of Reproductive Biology 1985;7:168-222.

Daniel SAJ, Armstrong DT. Androgens in the ovarian microenvironment. Seminars in Reproductive Endocrinology 1986;4(2):89-100.

Gore-Langton R, Armstrong D. Follicular steroidogenesis and its control. In: Knobil E, Neill J, eds. The Physiology of Reproduction. New York: Raven Press; 1988:331-85.

Yan Z, Lee GY, Anderson E. Influence of dehydroepiandrosterone on the expression of insulin-like growth factor-1 during cystogenesis in polycystic rat ovaries and in cultured rat granulosa cells. Biol Reprod 1997;57(6):1509-16.

Wang H, Andoh K, Hagiwara H, et al. Effect of Adrenal and Ovarian Androgens on Type 4 Follicles Unresponsive to FSH in Immature Mice. Endocrinology 2001;142(11):4930-6.

Hu Y-C, Wang P-H, Yeh S, et al. Subfertility and defective folliculogenesis in female mice lacking androgen receptor. PNAS 2004;101(31):11209-14.

Tetsuka M, Hillier SG. Differential regulation of aromatase and androgen receptor in granulosa cells. J Steroid Biochem Mol Biol 1997;61(3-6):233-9.

Hickey TE, Marrocco DL, Gilchrist RB, Norman RJ, Armstrong DT. Interactions Between Androgen and Growth Factors in Granulosa Cell Subtypes of Porcine Antral Follicles. Blot Reprod 2004;71(1):45-52.

Harlow CR, Hillier SG, Hodges JK. Androgen modulation of follicle-stimulation hormone-induced granulosa cell steroidogenesis in the primate ovary. Endocrinology 1986;119(3):1403-5.

Vendola K, Zhou J, Wang J, Famuyiwa OA, Bievre M, Bondy CA. Androgens Promote Oocyte Insulin-Like Growth Factor I Expression and Initiation of Follicle Development in the Primate Ovary. Biol Reprod 1999;61(2):353-7.

Horie K, Takakura K, Fujiwara H, Suginami H, Liao S. Mori T. Immunohistochemical localization of androgen receptor in the human ovary throughout the menstrual cycle in relation to oestrogen and progesterone receptor expression. Hum Reprod 1992;7(2):184-90.

Casson PR, Santoro N, Elkind-Hirsch K, et al. Postmenopausal dehydroepiandrosterone administration increases free insulin-like growth factor-I and decreases high-density lipoprotein: a six-month trial. Fertil Steril 1998;70(1):107-10.

Casson PR, Lindsay MS, Pisarska MD, Carson SA, Buster JE. Dehydroepiandrosterone supplementation augments ovarian stimulation in poor responders: a case series. Hum Reprod 2000;15(10):2129-32.

Frattarelli JL, Peterson EH. Effect of androgen levels on in vitro fertilization cycles. Fertil Steril 2004;81(6):1713-4.

Barbieri RL, Sluss PM, Powers RD, et al. Association of body mass index, age, and cigarette smoking with serum testosterone levels in cycling women undergoing in vitro fertilization. Fertil Steril 2005;83(2):302-8.

Mitwally MF, Casper RF. Aromatase inhibition improves ovarian response to folliclestimulating hormone in poor responders. Fertil Steril 2002;77(4):776-80.

MacDougall M, Tan S, Balen A, Jacobs H. A controlled study comparing patients with and without polycystic ovaries undergoing in-vitro fertilization. Hum Reprod 1993;8(2):233-7.

Maciel GAR, Baracat EC, Benda JA, et al. Stockpiling of Transitional and Classic Primary Follicles in Ovaries of Women with Polycystic Ovary Syndrome, J Clin Endocrinol Metab 2004;89(11):5321-7.

Amirikia H, Savoy-Moore RT, Sundareson AS, Moghissi KS. The effects of longterm androgen treatment on the ovary. Fertil Steril 1986;45(2):202-8.

van der Westhuizen S, van der Spuy ZM. Ovarian morphology as a predictor of hormonal values in polycystic ovary syndrome. Ultrasound Obstet Gynecol 1996;7(5):335-41.

Pache TD, Chadha S, Gooren LJ, et al. Ovarian morphology in long-term androgentreated female to male transsexuals. A human model for the study of polycystic ovarian syndrome? Histopathology 1991;19(5):445-52.

Kroboth PD, Salek FS, Pittenger AL, Fabian TJ, Frye RF. DHEA and DHEA-S: a review. J Clin Pharmacol 1999:39(4):327-48.

Kaaks R, Berrino F, Key T, et al. Serum Sex Steroids in Premenopausal Women and Breast Cancer Risk Within the European Prospective Investigation into Cancer and Nutrition (EPIC). J Natl Cancer Inst 2005;97(10):755-65.

McClamrock HD, Adashi EY. Gestational hyperandrogenism. Fertil Steril 1992;57(2):257-74.

Sir-Petermann T. Maliqueo M, Angel B, Lara HE, Perez-Bravo F, Recabarren SE. Maternal serum androgens in pregnant women with polycystic ovarian syndrome: possible implications in prenatal androgenization. Hum Reprod 2002;17(10):2573-9.

*Further Evidence that Dehydroepaindrosterone (DHEA) Substitution Improves Ovarian Function: Is 17,20 Desmolase Deficiency Cause of Premature Ovarian Aging?,* " Norbert Gleicher MD, David Barad MD MS Barad D, Gleicher N (2005) Increased oocyte production after treatment with dehydroepiandrosterone. Fertil Steril, in press. (Included in Paper 1, #14 above).

Barad D, Gleicher N (2005a) Dehydroepiandrosterone (DHEA) adjuvant treatment of ovulation induction for in vitro fertilization and embryo quality. Submitted for publication. (Paper 1).

Casson PR, Santoro N, Elkind-Hirsch K, et al. (1998) Postmenopausal dehydroepiandrosterone administration increases free insulin-like growth factor-I and decreases high-density lipoporotein: a six-month trial: Fertil Steril 70, 107-10 (Included in 0222-0002 IDS).

Casson PR, Lindsay MS, Pisarska MD, Carson SA, Buster JE (2000) Dehydroepiandrosterone supplementation augments ovarian stimulation in poor responders: a case series. Hum Reprod 15, 2129-32 (Included in Paper 1, #42 above).

Consortium, Autoimmune Polyendocrinopathy-Candidiasis-Ectodermal Dystrophy, (1997) An autoimmune disease, APECED, caused by mutations in a novel gene featuring two PHD-type zinc-finger domains. Nat Genet 17:399-405.

Garcia-Velasco JA, Moreno L, Pacheco A, Guillen A, Duque L, Requena A, Pellicer A (2005) Fertil Steril, 84:82-7.

Gleicher N (2005) Ovarian aging: Is there a "norm"? Contemp Ob/Gyn 50:65-75 Gleicher N, Barad D (2005) Race-based fertility therapy. Submitted for publication.

Grainger DA, Seifer DB, Frazier LM, Tjaden BL, Merril JC (2004) Racial disparity in clinical outcomes from women using advanced reproductive technology (ART): Analysis of 80,196 ART cycles from the SART database 1900 and 2000. Fertil Steril, 28/S-2:0-93.

Hillier SG, Whitelaw PF, Smyth CD (1994) Follicular oestrogen synthesis: The 'two-cell, tow gonadotrophin' model revisited. Molec Cellular Endocrin, 100:51-4.

Purcell KJ, Schembi M, Shen S, Croughman M, Fujimoto VY (2004) Asian ethnicity is associated with reduced pregnancy outcome with in vitro fertilization. Fertil Steril, 28:2" 2,0-98.

Speroff L, Glass RH, Kase NG (1999): Postmenopausal hormone therapy; In Clinical Gynecology Endocrinology and Infertility, 6$^{th}$ ed: Lippincott Williams & Wilkins, pp. 725-799.

Speroff L, Glass RH, Kase NG (1999a): Normal and abnormal sexual development; Idem, pp. 339-379.

Speroff L, Glass RH, Kase NG (1999b): Amenorrhea; Idem, pp. 421-485.

Winqvist 0, Gebre-Medhin G, Fustafsson J, Ritzen EM, Lundkvist 0, Karlson FA, Kampe 0 (1995) Identification of main gonadal autoantigens in patients with adrenal insufficiency associated ovarian failure. J Clin Endocrinol Metab 80:1717-23.

Chuang, CC et al., "Age is a better predictor of pregnancy potential than basal follicle-stimulating hormone levels in women undergoing in vitro fertilization," Fertility and Sterility, Jan. 2003, pp. 63-68, vol. 79, No. 1, Elsevier Science Inc., U.S.A.

Munne, S. et al., "Improved Implantation after preimplantation genetic diagnosis of aneuploidy," Reproductive BioMedicine Online, May 2003, pp. 91-97, vol. 7, No. 1.

Giranaroli, L. et al., "Will preimplantation genetic diagnosis assist patients with a poor prognosis to achieve pregnancy?" Human Reproduction, 1997, pp. 1762-1767, vol. 12, No. 8, European Society for Human Reproduction and Embryology, Belgium.

Karande, V. and Gleicher, N., "A rational approach to the management of low responders in in-vitro fertilization" Human Reproduction, 1999, pp. 1744-1748, vol. 14, No. 7, European Society for Human Reproduction and Embryology, Belgium.

Paulus, W., et al., "Influence of acupuncture on the pregnancy rate in patients who undergo assisted reproduction therapy," Fertility and Sterility, Apr. 2002, vol. 77, No. 4, Elsevier Science Inc., U.S.A (printed from Easternharmonyclinic.com: Medical Article #7).

Casson, P.R., et al., "Dehydroepiandrosterone supplementation augments ovarian stimulation in poor responders: a case series," Human Reproduction, 2000, pp. 2129-2132, vol. 15, No. 10, European Society for Human Reproduction and Embryolog, Belgium.

Frattarelli and Peterson, "Effect of androgen levels on in vitro fertilization cycles," Fertility and Sterility, Jun. 2004, vol. 81, No. 6, Bsevler Science Inc., U.S.A.

Faddy, M.J., "Follicle dynamics during ovarian ageing," Molecular and Cellular Endocrinology, 2000, pp. 42-48, vol. 163, Elsevier Science Ireland Ltd.

Filicori, M., "The role of luteinizing hormone in folliculogenesis and ovulation induction," Fertility and Sterility. Mar. 1999. pp. 405-414, vol. 71, No. 3, Elsevier Science Inc., U.S.A.

Franks, S. et. al, "Follicular dynamics in the polycystic ovary syndrome," Molecular and Cellular Endocrinology, 2000. pp. 49-52, vol. 183, Elsevier Science Ireland Ltd.

Burger, H., "Androgen production in women," Fertility and Sterility, Apr. 2002, pp. S3-S5. vol. 77, No. 4, Suppl 4. Elsevier Science Inc., U.S.A.

Anderson, E., "Polycystic ovarian condition in the dehydroepiandrosterone-treated rat model: hyperandrogenism and the resumption of meiosis are major initial events associated with cyctogenesis of antral follicles," Anatomical Record. 249, pp. 44-53, 1997, Wiley-Liss, Inc.

Johnson, J., et. al., "Germline stem cells and follicular renewal in the postnatal mammalian ovary," Nature, Mar. 2004, pp. 145-150, vol. 428, Nature Publishing Group, Boston, Massachusetts.

Haning, R., et al., "Plasma dehydroepiandrosterone sulfate serves as a prehormone for 48% of follicular fluid testosterone during treatment with menotropins," Journal of Clinical Endocrinology and Metabolism, 1993, pp. 1301-1307, vol. 76, No. 5, JCE & M, U.S.A.

Casson, P., et. al., "Postmenopausal dehydroeplandrosterone administration increases free insulin-like growth factor-I and decreases high-density lipoprotein: a six month trial," Fertility and Sterility, Jul. 1998, pp. 107-110, vol. 428, No. 1, Elsevier Science Inc., U.S.A.

Kloza, B., et. al., "New fertility boast," ScienCentralNews, Oct. 13, 2004, pp. 1-4, ScienCentral Inc., USA.

Orvieto, R., et. al., "Results of in vitro fertilization cycles in women aged 43-45 years," Gynecol Endocrinol, 2003, pp. 75-78, vol. 18, No. 2.

"Aging and Infertility in women: a committee opinion," Fertil Steril, 2002, pp. 215-219, vol. 78, No. 1.

Kupesic, S., et. al., "Three-dimensional ultrasonographic ovarian measurements and in vitro fertilization outcome are related to age," Fertil Steril, 1999, pp. 190-197, vol. 79, No. 1.

Kroboth PD., et. al., "DHEA and DHEA-S: a review," J Clin Pharmacol, 1999, pp. 327-348, vol. 39, No. 4.

Roy, S., et. al., "The effect of dehydroepiandrosterone and D4-androstenedione on the reproductive organs of female rats: Production of cystic changes in the ovary," Nature, 1962, pp. 42-43, vol. 196.

Amirikia, H., et. al., "The effects of long-term androgen treatment on the ovary," Fertil Steril , 1986, pp. 202-208, vol. 45, No. 2.

Note—See Non-Patent Literature Documents Previously Submitted With U.S. Appl. No. 10/973,192.

* cited by examiner

Figure 1

| DHEA use | Cycle | Date | Cycle Day 3 FSH ml/Uml | Cycle Day 3 Estradiol pg/ml | Peak Estradiol pg/ml | Total Oocytes # | Total Oocytes Mean ± SD[1] | Mature oocyte # | 2pn | Day 3 embryos # | Cryopreserved Mean ± SD[2] |
|---|---|---|---|---|---|---|---|---|---|---|---|
| Early[3] | 1 | 09/03 | 10.59 | 18 | 330 | 1 | 2 ± 1.4 | 1 | 1 | 1 | 2.0 ± 1.4 |
| | 2 | 11/03 | 8.11 | 48 | 619 | 3 | | 3 | 3 | 3 | |
| Mid | 3 | 12/03 | 1.99 | 26 | 975 | 5 | 5.7 ± 1.2 | 5 | 5 | 5 | 5.3 ± 0.6 |
| | 4 | 01/04 | 15.18 | 5 | 908 | 7 | | 7 | 6 | 6 | |
| | 5 | 02/04 | 3.43 | 76 | 901 | 5 | | 5 | 5 | 5 | |
| Late | 6 | 03/04 | 4.96 | 70 | 3251 | 13 | 16.0 ± 3.0 | 12 | 9 | 9 | 10.0 ± 1.0 |
| | 7 | 05/04 | 1.70 | 42 | 3150 | 16 | | 12 | 10 | 10 | |
| | 8 | 06/04 | 2.42 | 75 | 5055 | 19 | | 16 | 13 | 11 | |

[1] (*early & mid*) vs. *late*, p = 0.0001; *early* vs. *mid*, ns; Linear trend across group F=51.9; 1 df; p = 0.001
[2] (*early & mid*) vs. *late*, p < 0.001; *early* vs. *mid*, p = 0.01; Linear trend across group F=82.3; 1 df; p < 0.001
[3] DHEA treatment began 2 weeks before the start of the second cycle on October 6, 2003.

Figure 5: Adrenal function of 17, 20 desmolase (P450c17) *
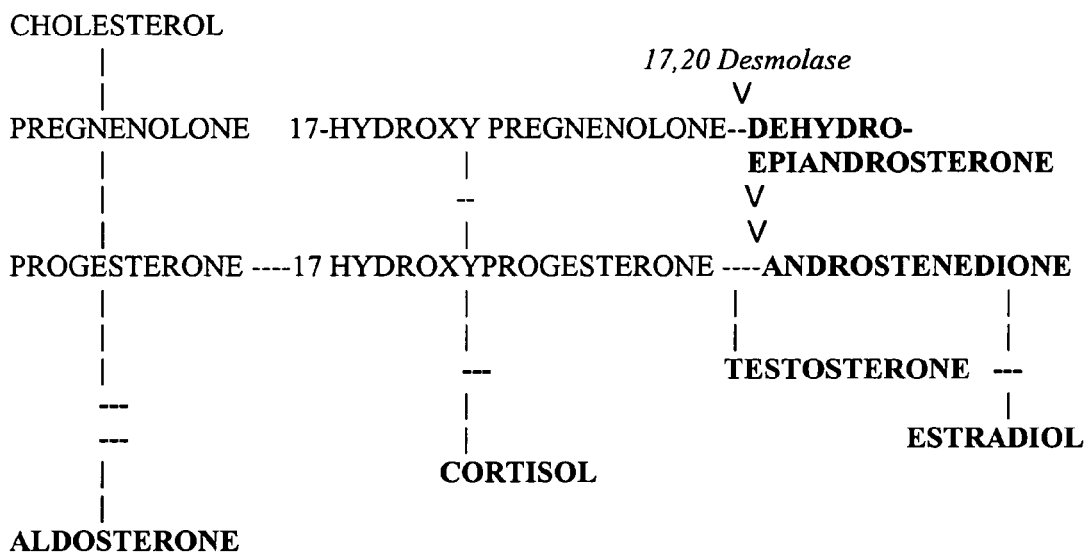
*Modified from Speroff et al., (1999a); Cytochrome P450 is a generic term used for a group of oxidative enzymes active in steroidogenesis. P450c17 is the enzyme mediating 17-hydroxylas and 17, 20- lyase.

METHOD OF IMPROVING CUMULATIVE EMBRYO SCORE AND QUANTITY OF FERTILIZED OOCYTES, INCREASING EUPLOIDY RATE AND OF NORMALIZING OVARIAN FUNCTION USING AN ANDROGEN SUCH AS DEHYDROEPIANDROSTERONE

This application is a continuation-in-part of application Ser. No. 10/973,192 filed on Oct. 26, 2004 now abandoned.

BACKGROUND OF THE INVENTION

1. Field of the Invention

The present invention relates to a method of improving ovulation induction and embryo quality in women undergoing in vitro fertilization and other infertility treatments involving administering an androgen such as dehydroepiandrosterone prior to or during ovulation stimulation cycles.

2. Description of the Related Art

The application of assisted reproductive technology has revolutionized the treatment of all forms of infertility. The most common assisted reproductive technology is in vitro fertilization (IVF), in which a woman's eggs are harvested and fertilized with a man's sperm in a laboratory. Embryos grown from the sperm and eggs are then chosen to be transferred into the woman's uterus. Assisted reproductive technology in women depends on ovarian stimulation and concurrent multiple oocyte development, induced by exogenous gonadotropins.

Infertile women are often treated with gonadotropin treatments such as gonadotropin-releasing hormone (GnRH) flare protocols. Estrogen pre-treatment with concomitant growth hormone (GH) treatment is sometimes used in an effort to try and amplify intra-ovarian insulin-like growth factor-I (IGF-I) paracrine effect, which is expressed by granulosa cells and enhances gonadotropin action. However, the clinical utility of combined GH/ovarian stimulation is limited and responses are not dramatic.

Dehydroepiandrosterone (DHEA) is secreted by the adrenal cortex, central nervous system and the ovarian theca cells and is converted in peripheral tissue to more active forms of androgen or estrogen. DHEA secretion during childhood is minimal but it increases at adrenarche and peaks around age 25, the age of maximum fertility, only to reach a nadir after age 60. There is evidence to support use of exogenous DHEA to increase ovulation stimulation in older women who respond poorly to gonadotropin treatments. First, studies demonstrate marked augmentation of serum IGF-I concentrations of oral administration of physiological DHEA. Second, DHEA is a steroid prohormone for ovarian follicular sex steroidogenesis.

Third, Casson studies have shown that concurrent oral DHEA supplementation over about two months and one or two stimulation cycles improved gonadotropin response by approximately two-fold in women who had normal follicular stimulating hormone concentrations, yet had poor response to ovarian stimulation. Frattarelli and Peterson found that cycle day 3 testosterone above 20 ng/dL was associated with higher IVF pregnancy rates (11.2% vs. 53.1%). Approximately 25 to 50 mg of DHEA is considered physiologic replacement for young females. Adverse effects are extremely uncommon at such dosages, while dosages as high as 1600 mg daily have caused significant side effects, requiring discontinuation of treatment.

The "aging ovary" represents the last frontier of human infertility treatment and is generally considered untreatable with current medical resources. The possibility that any intervention may significantly benefit the response of the aging ovary is therefore potentially revolutionary. The studies show many ways in which ovulation induction can be improved in infertile women. These studies show DHEA as possible, but not preferred, treatments for improving ovulation induction.

BRIEF SUMMARY OF THE INVENTION

The present invention is directed to the administration of an androgen for at least about four consecutive months, to precondition ovulation induction in women. In one embodiment, the androgen is dehydroepiandrosterone (DHEA). DHEA administration may be conducted orally in patients. In conjunction with DHEA, high dose gonadotropins may be administered. Also in conjunction with DHEA, follicle stimulating hormone (FSH), norethindrone acetate, leuprolide acetate, and gonadotropin may be used to maximize ovulation induction.

In another aspect of the invention, a method of improving cumulative embryo score may comprise administering an androgen to a human female, for example, DHEA, for at least about four consecutive months followed by harvesting and fertilizing oocytes and forming embryos. Between about 50 mg and about 100 mg of DHEA may be administered to a human female per day. Moreover, a method of increasing the quantity of fertilized oocytes may comprise administering an androgen to a human female for at least about four consecutive months, harvesting and fertilizing the oocytes. Furthermore, a method of increasing the quantity of day 3 embryos from one cycle of in vitro fertilization may comprise administering an androgen for at least about four consecutive months, harvesting and fertilizing the oocytes and forming day 3 embryos.

In a further aspect, the invention relates to methods of normalizing ovarian DHEA levels by administering an androgen to a human female for at least about four consecutive months. In a still further aspect, the invention relates to increasing euploidy rate in embryos, by administering an androgen to a human female for at least about four consecutive weeks.

BRIEF DESCRIPTION OF THE DRAWINGS

FIG. 1 is a table showing improved ovulation induction with DHEA.

FIG. 5 is a chart showing chemical pathways of adrenal function.

DETAILED DESCRIPTION OF THE INVENTION

Figure 2:
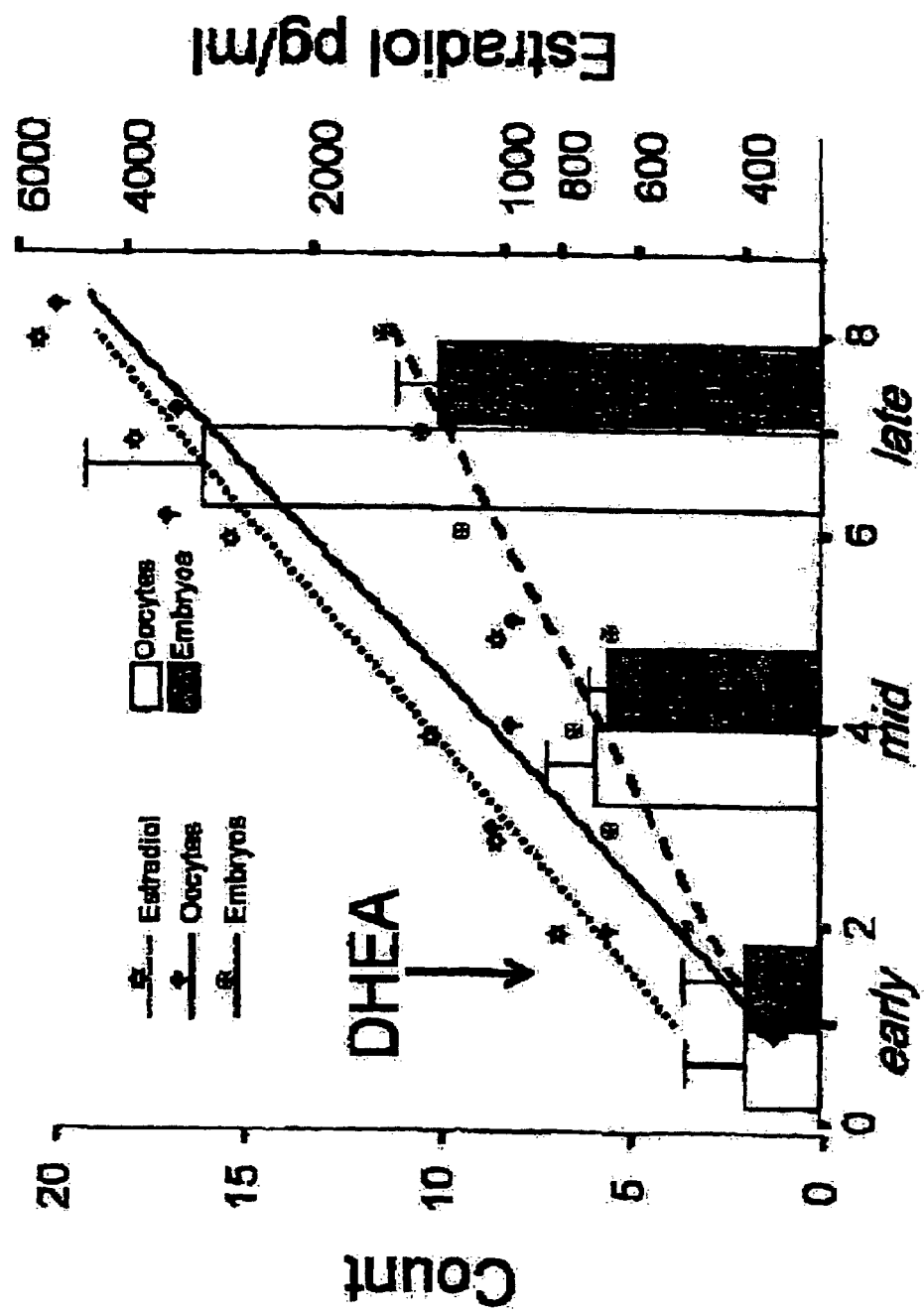
FIG. 2 is a graph showing increase in the number of fertilized oocytes resulting from oocytes harvested from women with DHEA treatment.

When attempting in vitro fertilization, older women produce few oocytes and yield few normal embryos, even when exposed to maximal gonadotropin stimulation. The decreased ability of older women to respond to ovulation inducing medications is evidence that ovarian reserve declines with age. The ability of women to respond to ovulation inducing medications declines with age. With IVF cycles, older women produce few oocytes and yield few normal embryos when exposed to maximal gonadotropin stimulation. This change in ovarian responsiveness is known as diminished ovarian reserve.

The reservoir of primordial follicles is steadily depleted throughout life. The transition from primary follicle to pre-antral follicle can take between about four and about six months. On the way, atresia and apoptosis are responsible for the disappearance of most follicles that have initially been recruited in a cycle. As follicles grow they move through the stages of primary, preantral, antral, and preovulatory follicles and finally to ovulation. The majority of follicles end in hormonally controlled apoptosis known as atresia, only a few ever mature to ovulation. A change in follicular dynamics with improved survival of follicles to the early antral stages, when gonadotropin dependent cyclic recruitment can influence further follicular growth may be one potential mechanism by which DHEA affects oocyte quantity and quality.

Androgens can influence ovarian follicular growth either by acting as metabolic precursors for steroid production, as ligands for androgen receptors or by some non-classical mechanism. Adrenal androgen and androgens produced by the theca cell act as prehormones for granulose cell production of estradiol. Human granulose cells are a site of sulfatase activity and dehydroepiandrosterone-sulfatase (DHEAS) and DHEA can be utilized as a substrate for androstenedione and estrogen production. During ovulation induction with exogenous gonadotropins DHEA is the prehormone for up to about 48% of follicular fluid testosterone, which is itself the prehormone for estradiol.

Androgens act together with follicle stimulating hormone (FSH) to stimulate follicular differentiation. Insulin-like growth factor-1 (IGF-1) expression is higher in preantral and early antral follicles of DHEA treated rat ovaries. In vitro cultured murine preantral follicles increase follicle size and DNA synthesis in response to androgens but not to estrogens. Preantral murine follicles are unresponsive to recombinant human follicle stimulating hormone (rFSH) but respond synergistically to combinations of androgen and rFSH. Mice lacking androgen receptor have impaired fertility and evidence of defective early folliculogenesis. In rodents androgens enhance recruitment of primordial follicles into the growth pool but cause atresia of late antral follicles.

The potent androgen receptor agonist dihydrotestosterone (DHT) stimulates proliferation of porcine granulose cells and inhibits progesterone production. The action of DHT in porcine follicles was greater in about 1 mm to about 3 mm follicles than in about 3 mm to about 5 mm diameter follicles. Androgens are known to promote steroidogenesis, follicular recruitment and to increase insulin like growth factor in the primate ovary. Androgen receptors are absent in human primordial and primary follicles but there is evidence of nuclear staining for androgen receptor in human granulose and thecal cells in secondary follicles.

Improved IVF outcomes are reported among women with higher baseline testosterone levels. Higher serum testosterone is correlated with higher estradiol and oocyte numbers retrieved for IVF. Improved outcomes in women with diminished ovarian reserve after co-treatment with an aromatase inhibitor during cycle stimulation may be the consequence of FSH induction. The resultant ovarian response then leads to improved follicular survival, increased follicle numbers and higher estradiol levels during stimulation, as also observed in polycystic ovarian disease.

It is possible that DHEA treatment may create polycystic ovaries (PCO)-like characteristics in the aging ovary. Human PCO's have been described as representing a "stock-piling" of primary follicles secondary to an alteration at the transition from primordial to primary follicle. Possible mechanisms suggested for this observation are abnormal growth factors, increased LH, or increased ovarian androgen. Normal ovarian theca cells of the pre-antral follicle produce androstenedione, DHEA, and testosterone. Women with polycystic ovaries have higher serum testosterone, androstenedione and DHEA compared to controls and higher ovarian venous levels of DHEA, androsterone and testosterone. Long term exogenous androgen exposure can induce PCO like histological and sonographic changes in normal ovaries similar to PCO.

DHEA may be administered to a human female at a dose of between about 50 mg/day and about 100 mg/day, preferably between about 60 mg/day and about 80 mg/day, and in one study about 75 mg/day. DHEA may have an effect on women after about 4 weeks, but the effect may increase over time. DHEA effects may reach statistically significant effects after about 4 months of use, but may continue to increase past four months of use. In one study, ovulation induction was accomplished with norethindrone acetate, leuprolide acetate, human menopausal gonadotropin, and follicle-stimulating hormone.

A DHEA dose of about 1600 mg daily may result in significant adverse effects, often requiring the discontinuation of the medication. The safety issue of most concern is that DHEA—as a precursor of sex steroids—may increase the risk of estrogen- or androgen-dependent malignancies. Pregnancy, in itself, is a high androgen state, and women with polycystic ovarian diseases, also a high androgen state, do not generally deliver daughters with masculinized external genitalia. This suggests that the limited and low-dosage use of DHEA in infertility patients should be safe. DHEA is currently available in the U.S. without prescription.

Possible side effects associated with DHEA use are acne, deepening voice and facial hair growth, though long-term effects of DHEA administration are unknown. As a precursor of sex steroids one, of course, has to be concerned abut the potential effect on hormone-sensitive malignancies.

I. Improvements in Ovulation

Treatments with an androgen, alone or in conjunction with other hormones, increase a woman's response to ovulation induction, measured in both oocyte and embryo yield. Androgens may be, for example, dehydroepiandrosterone (DHEA) or testosterone. DHEA treatment is an adjunct to ovulation induction. DHEA taken orally for at least about four months before initiating gonadotropin treatment may prepare the ovaries for gonadotropin stimulation. It is believed that a larger response may be obtainable by combining gonadotropins and DHEA in treatment over an at least about four month period before an IVF cycle.

Young ovaries are characterized by large numbers of antral follicles and a low rate of atresia. In contrast, older ovaries have few antral follicles, high rates of atresia and exhibit increasing "resistance" to ovulation induction. With IVF, older women have decreased oocyte quantity and quality, produce fewer high quality embryos and have lower implantation and pregnancy rates. Most follicular atresia occurs after the primordial follicle resumes growth but before it is gonadotropin responsive enough for recruitment. An induced delay in onset of atresia may salvage follicles for possible ovulation. Interestingly, such an "arrest" of the atretic process has been noted among anovulatory women with polycystic ovary syndrome (PCO). For these women follicles remain steroidogenicaly competent and show evidence of increased aromatase activity compared to like-sized follicles from normal ovaries. Follicular hypersecretion of DHEA, which is typical of PCO, is associated with increased aromatase activity. The increased yield of oocytes and embryos experienced by patients undergoing DHEA treatment also suggest this underlying physiological process.

II. Improvements to Cumulative Embryo Score

DHEA use may have a beneficial effect on oocyte and embryo quality. The observation that DHEA treatment was associated with improved cumulative embryo scores may infer that such treatment leads to improved embryo and egg quality. This suggestion is further supported by strong trends towards improved euploidy in embryos and improved pregnancy rates.

Cumulative embryo score is determined by multiplying the number of cells in the embryo by the embryo grade. Embryo grade is a judgment of the embryologist on embryo quality from 1 to 5. Most good embryos are scored 4, with 5 reserved for exceptional embryos. The grade is based on the uniformity of the cells, the color and consistency of the cytoplasm, and the amount of fragmentation. Normal embryos are less than 5% fragmented. A woman with three eight cell embryos each with a grade of four would have a cumulative embryos score of 96, the product of 3×8×4.

A cumulative embryo score for women prior to DHEA use may have been about 34. A cumulative embryo score after DHEA use of at least about four consecutive months may be at least about 90, preferably at least about 95, and in one study at least about 98. The increase in cumulative embryo score may be at least about 56, preferably at least about 60, and in one study about 64. The difference in the cumulative embryo score prior to DHEA use and the cumulative embryo score after DHEA use may be statistically significant, $p<0.001$.

III. Increase in the Number of Fertilized Oocytes

Figure 3:
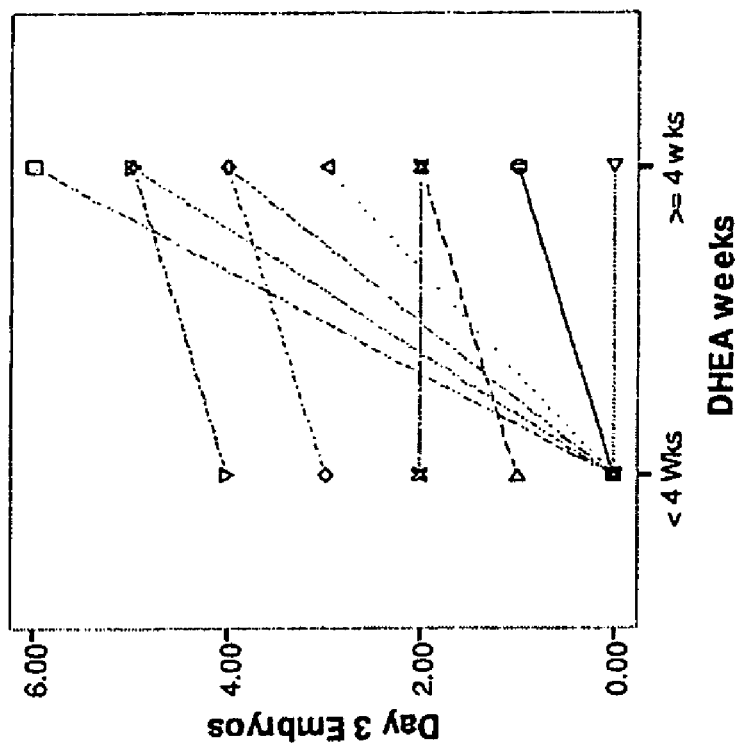
FIG. 3 is a graph showing increase in the number fertilized oocytes resulting from oocytes harvested from women with at least 4 weeks of DHEA treatment.

The number of fertilized oocytes produced by women significantly increased after at least about 4 months of consecutive DHEA treatment in 12 women, even though slight improvements were shown after at least about four weeks of consecutive DHEA treatment, as shown in FIG. 3. As shown in FIG. 3, paired comparisons of fertilized oocytes from women having less than about four consecutive weeks of DHEA treatment to the same women having at least about four consecutive weeks of DHEA treatment showed an increase of about 2 fertilized oocytes, or a median increase of about 2.5 fertilized oocytes. The number of fertilized oocytes may show more significant increase after at least about 4 months of DHEA treatment, and may show maximal increase after at least about eight months of DHEA treatment.

IV. Increase in the Number of Day 3 Embryos

Figure 4:
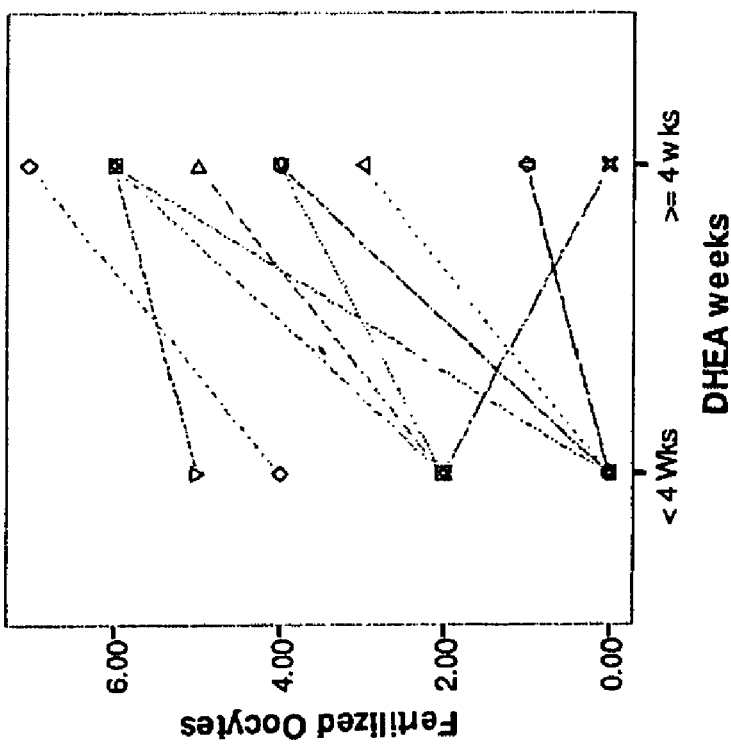
FIG. 4 is a graph showing an increase in the number of day three embryos resulting from oocytes harvested from women with at least 4 weeks of DHEA treatment.

The number of day 3 embryos produced by women also may significantly increase after at least about four months of consecutive DHEA treatment in 12 women, even though slight increases may be shown after at least about 4 weeks of DHEA treatment, as shown in FIG. 4. All of the day 3 embryos included in the study were normal based on their appearance and on the number of cells, i.e. at least four cells. Paired comparisons of fertilized oocytes from women having less than about four consecutive weeks of DHEA treatment to the same women having at least about four consecutive weeks of DHEA treatment may show an increase of about 1 day 3 embryo, and in the study summarized in FIG. 4, an increase of about 2 day 3 embryos. While the number of day 3 embryos produced slightly increased after at least 4 weeks of DHEA treatment, more significant increase occurs after at least about 4 months of DHEA treatment, and maximal increase may occur after at least about eight months of DHEA treatment.

V. Improvements to Ovarian Function

As shown in FIG. 5, the adrenal enzyme 17,20-desmolase may be responsible for the conversion of 17-hydroxy pregnelonone into dehydroepiandrosterone (DHEA) (and the conversion of 17-hydroxyprogesterone into androstenedione) which, based on the two-cell two-gonadotropin theory, may serve in the ovary as a precursor substrate for estradiol and androgens. DHEA substitution may rejuvenate certain aspects of ovarian function in older ovaries. Since DHEA declines with age to a very significant degree, intraovarian DHEA deficiency may be causally related to the ovarian aging process.

DHEA may have beneficial effects on ovarian function, and oocyte and embryo quality. How DHEA exerts these effects on the female ovary has remained open to speculation. Casson et al suggested that it may occur through an increase in insulin-like growth factor-I within the intraovarian environment (Casson et al., 1998). Others have suggested that the intraovarian increase in androgens, by itself, may improve ovarian response to stimulation, possibly by improving the sensitivity of FSH receptors on granulose cells. (Garcia-Velasco et al., 2005). We have suggested that, based on the two-cell, two-gonadotropin model (Hillier et al., 1994), DHEA serves as substrate for the production of estradiol. Since DHEA significantly declines with age (Speroff et al., 1999), this substrate decreases, resulting in lower estradiol (and androgen) levels after ovarian stimulation with gonadotropins (Barad and Gleicher, 2005 and 2005a). DHEA substitution would then be expected to reverse the deficiency in substrate and, therefore, increase estradiol (and androgen) levels.

FIG. 5 shows the pathways for normal adrenal function. A patient with abnormal 17,20 desmolase (P450c17) function may have a hormone profile characterized by persistently low DHEA, androstenedione, testosterone and estradiol levels, but normal aldosterone and cortisol levels. The patient exhibited some of the classical signs of prematurely aging ovaries (Nikolaou and Templeton, 2003; Gleicher N, 2004) which include ovarian resistance to stimulation, poor egg and embryo quality and prematurely elevated FSH levels.

We have previously suggested that the decrease in DHEA levels, with advancing female age, may be an inherent part of the ovarian aging process and may, at least in part, and on a temporary basis, be reversed by external DHEA substitution (Barad and Gleicher, 2005). This case demonstrates that low DHEA levels are, indeed, associated with all the classical signs of (prematurely) aging ovaries. While association does not necessarily suggest causation, the observed sequence of events in this patient supports the notion that low DHEA levels adversely affect ovarian function.

The patient was initially thought to have largely unexplained infertility. Approximately 10 percent of the female population is believed to suffer from premature aging ovaries and this diagnosis is often mistaken for unexplained infertility (Nikolaou and Templeton, 2003, Gleicher N, 2005). The patient later developed signs of prematurely aging ovaries and, finally, even showed elevated FSH levels. In the time sequence, in which all of these observations were made, the patient followed the classical parallel, premature aging curve (Nikolaou and Templeton, 2003; Gleicher N, 2005).

Once substituted with oral DHEA a reversal of many findings characteristic of the aging ovary was noted. First, the patient's DHEA and DHEAS levels normalized. In subsequent natural cycles an apparently normal spontaneous follicular response was observed, with normal ovulatory estradiol levels in a patient with persistently low estradiol levels before DHEA treatment (Table 2). The response to ovarian stimulation improved, quantitatively and qualitatively, as the patient improved peak estradiol levels, oocyte and embryo numbers and, as the successful pregnancy may suggest, also embryo quality.

DHEA deficiency may be a cause of female infertility and may be a possible causative agent in the aging processes of the ovary. It also presents further confirmation of the value of DHEA substitution whenever the suspicion exists that ovaries may be lacking of DHEA substrate. Since the process is familial (Nikolaou and Templeton, 2003), it is reasonable to assume that, like other adrenal enzymatic defects, 17,20-desmolase deficiency, may occur either in sporadic or in an inherited form. As both forms will result in abnormally low DHEA levels, both may lead to phenotypical expression as premature ovarian aging.

That there may be a genetic component to the aging process of ovaries has also been suggested by recent observations of IVF outcomes in different racial groups which offer evidence that the physiological aging curves in African American and Asian, in comparison to Caucasian, women may be shifted towards younger age (Grainger et al., 2004; Purcell et al., 2004; Gleicher and Barad, 2005).

VI. Increase in Spontaneous Conceptions

After DHEA treatment, there may be an unexpectedly large number of spontaneous conceptions in women waiting to go into an IVF cycle. The DHEA treatment may be at least about 2 weeks before spontaneous conception occurs. In the population of women who are waiting to go into IVF, the spontaneous pregnancy rate is a fraction of 1% per month. However, in the population of women who have been on DHEA treatment, there were 13 spontaneous pregnancies out of 60 women, or about 22%. This may provide evidence that DHEA works not only in conjunction with gonadotropin stimulation of ovaries, but also without gonadotropin stimulation of ovaries.

EXAMPLE 1

Improved Ovulation

A 43 year old woman undergoing IVF with banking of multiple cryopreserved embryos for future aneuploidy screen and transfer is administered an androgen, namely DHEA. In ten months she undergoes eight treatment stimulation cycles while continuously improving her ovarian response, resulting in oocyte and embryo yields far beyond those previously seen in a woman her age.

The patient's history is unremarkable except for two previous malarial infections. She is allergic to sulfa medications and has a history of environmental allergies. Her surgical history includes umbilical hernia repair at age one and cholecystectomy at age 21. She had used oral contraceptives for over 10 years. She has no history of irregular menstrual cycles.

Day three serum FSH and estradiol (E2) in her first IVF cycle are 11 mIU/ml and 18 pg/ml, respectively. In subsequent cycles her baseline FSH is as high as 15 mIU/ml. She is given an ovulation induction protocol which is prescribed for patients with evidence of decreased ovarian reserve. Briefly, the protocol includes the following medications: norethindrone acetate tablets (10 mg) for 10 days, starting on day two of menses, followed three days later by a "microdose" dosage of 40 μg of leuprolide acetate, twice daily, and, after another three days, by 600 IU of FSH (Gonal-F; Ares-Serono, Geneva, Switzerland) daily. Peak serum E2 concentration on day nine of stimulation is 330 pg/ml. Following injection of 10,000 IU human chorionic gonadotropin (hCG), she undergoes oocyte retrieval. Only one oocyte is obtained and one embryo is cryopreserved.

Because of the poor response to ovulation stimulation, she is advised to consider donor oocyte or embryo donation. She rejects both options. She starts a second cycle using the same stimulation protocol with one exception: instead of 600 IU of FHS daily, the patient received 450 IU of FSH and 150 IU of human menopausal gonadotropin (HMG, Pergonal, Ares-Serono, Geneva, Switzerland). This stimulation protocol is continued in identical fashion for the remaining cycles. However, two weeks before starting her second cycle, she begins administration of 75 mg per day of oral micronized DHEA. The date on which she begins administration of 75 mg per day of oral micronized DHEA is Oct. 6, 2003.

Methods

The eight treatment cycles are divided into three groups to allow statistical comparison: pre-initiation and very early use of DHEA (early=cycles 1 and 2), initial cycles (mid=cycles 3-5), and later cycles (late=cycles 6-8). Comparison between these categories is by one-way analysis of variance (ANOVA) and multiple comparisons by Student-Neuman-Keuls (SNK) test. The homogeneity of variances and used orthogonal linear contrasts are tested to compare groups and polynomial contrast to test for linear and quadratic trends. All outcomes are presented as mean±1 standard deviation. Rate of change of oocyte counts, cryopreserved embryos and (log transformed) peak estradiol between subsequent cycles is estimated by linear regression.

Embryos are evaluated by the embryologists on day three post-insemination for cell-count and grading. Embryo grading is based on a 1 to 4 scale depending on symmetry, percent fragmentation and appearance of the cytoplasm. All viable embryos are cryopreserved. Statistics are performed using SPSS for Windows, Standard version 10.0.7 (SPSS Co., Chicago, Ill.). Assay of E2 and FSH are performed using the ACS: 180 chemoluminescence system (Bayer Health Care LLC, Tarrytown, N.Y.).

A method of preconditioning ovulation induction in a human female is conceived, comprising administering an androgen in a female for at least about four consecutive months. In one embodiment, the androgen is DHEA. Administration of DHEA for at least about four consecutive months may further comprise administering high dose gonadotropins to the female. Furthermore, DHEA may be administered along with follicle stimulating hormone, human menopausal gonadotropin, norethindrone acetate, leuprolide acetate, and human chorionic gonadotropin. DHEA may be administered orally.

The length of time the androgen is administered to the female can be at least four consecutive months. The DHEA treatment may continue for more than four months. In one embodiment, the androgen administered is DHEA.

Results

The results of ovulation induction are displayed in FIG. 1. After eight stimulation cycles and approximately eight months of DHEA treatment, the patient produced 19 oocytes and 11 cryopreservable embryos. A total of 50 viable embryos have so far been cryopreserved. Significantly more oocytes ($p=0.001$) and cryopreserved embryos ($p<0.001$) are obtained in the late cycles (cycles 6-8, 4+consecutive months of DHEA treatment) compared to the combined early and mid cycles (cycles 1-5, 0-4 consecutive months of DHEA treatment). There is no significant difference in average embryo cell count (6.83±1.37 vs. 7.2±1.15) or morphology (3.6±0.5 vs. 3.7±0.5) between early and mid compared to late cycles. Peak E2, total oocyte, and embryos cryopreserved increase linearly from cycle to cycle, as shown in FIG. 1. Oocyte yield increase 2.5±0.34 oocytes per cycle ($p<0.001$), cryopreservable embryo yield increase 1.4±0.14 embryos per cycle (p<0.001) and (log) peak E2 increase 0.47±0.06 (p<0.001) across treatment cycles.

The linear increase in (log) peak E2 shown in FIG. 2 represents a cycle to cycle rate of increase from 123 pg/ml/cycle to 1491 pg/ml/cycle over the eight cycles of treatment. After adjusting for cycle day, the (harmonic) mean E2 is 267 pg/ml (95% confidence intervals (CI) 143 to 498 pg/ml) in the early phase, 941 pg/ml (95% CI 518 to 1712 pg/ml) in the mid phase, and 1780 pg/ml (95% CI 1121 to 2827 pg/ml) in the late phase of treatment. Each of these homogeneous subsets is significantly different from the other (p<0.05) by SNK multiple comparison testing.

The dramatic increase in oocyte and embryo yield experienced by this 43 year old woman is completely surprising and unexpected. The patient's post-DHEA response to ovulation induction has become more like that of a younger woman with PCO, than that of a 43 year old woman. Since starting DHEA treatment, the patient has produced 49 embryos of high enough quality to undergo cryopreservation. Sixty percent of those embryos were produced in the last three cycles of treatment, which took place after at least about four consecutive months after starting treatment. After producing only one embryo prior to starting DHEA treatment, the patient improved by an order of magnitude and produced 13 oocytes and 9 embryos in a cycle after at least about four consecutive months of DHEA treatment, 16 oocytes and 10 embryos in a cycle after at least about five and a half consecutive months of DHEA treatment, and 19 oocytes and 11 embryos in a cycle after at least about seven consecutive months of DHEA treatment.

The increasing numbers of cryopreservable embryos may suggest that embryo quality has improved. Quantity of embryos definitely is improved and quality may be improved. This patient also took high dose gonadotropins along with DHEA for several months.

The preceding example is to be construed as merely illustrative and not limitative of the remainder of the disclosure in any way.

EXAMPLE 2

Improved Oocyte Fertilization and Cumulative Embryo Score

Thirty (30) patients with evidence of decreased ovarian reserve were given supplemental dehydroepiandrosterone (DHEA) 25 mg three times a day, for a total of 75 mg per day, for an average of about 4 months before beginning ovulation induction for IVF. Twelve patients contributed data from cycles both pre-DHEA and post-DHEA, eleven patients contributed data from cycles only pre-DHEA, and seven patients contributed data from cycles only post-DHEA. Patients' response to ovulation induction before DHEA treatment was compared to patients' response to ovulation induction after DHEA treatment with regard to peak estradiol, oocyte production, and embryos transferred and embryo quality.

The thirty patients contributed to data for 42 total cycles, 23 cycles prior to and 19 cycles after starting DHEA supplementation. In comparing the patients as a group pre- and post-DHEA treatment cycles, there were improvements in cancellation rate, peak estradiol, average day 3 embryo cell counts, and embryo grade, but the improvements were not statistically significant. However, average oocyte numbers, eggs fertilized, day-three embryos, embryos transferred and cumulative embryo scores increased significantly after DHEA treatment. In logistic regression models adjusted for oocyte number, there was evidence of improved fertilization rates (p<0.005), increased numbers of 1 day-three embryos (p<0.05), and of improved overall embryo score (p<0.01). In 34 IVF cycles that reached the embryo transfer stage, a positive pregnancy test was obtained in zero of 16 cycles with less than an average of about 4 months of DHEA treatment and in 4/18 (22%) cycles after an average of 4 months of DHEA treatment.

This case series illustrates the possibility that some ovarian function can be salvaged, even in women of advanced reproductive age.

TABLE 1

Univariate comparison of results of in vitro fertililization before and after treatment with DHEA.

| | Pre DHEA | Post DHEA | p |
|---|---|---|---|
| N | 23 | 19 | |
| Age | 40.9 ± 0.7 | 42.8 ± 0.7 | ns |
| Weeks of DHEA | — | 16.1 ± 2.4 | — |
| Cancellation | 5/21 (21%) | 1/19 (5%) | ns |
| Peak Estradiol | 1018 ± 160 | 1192 ± 904 | ns |
| Oocytes | 3.3 ± 0.7 | 5.8 ± 1.0 | 0.04 |
| Fertilized eggs | 1.3 ± 0.3 | 4.6 ± 0.8 | <0.001 |
| Average Day 3 embryo cell count | 3.1 ± 0.6 | 4.5 ± 0.5 | ns |
| Average Day 3 embryo grade | 2.4 ± 0.3 | 2.8 ± 0.3 | ns |
| Cumulative Embryo Score | 34 ± 6.8 | 98 ± 17.5 | 0.001 |
| Transferred embryos | 1.0 ± 0.2 | 2.6 ± 0.4 | 0.001 |
| Number of Day 3 embryos 0.9 ± 0.2 | 3.2 ± 0.6 | 0.001 | |
| Positive hCG (per transfer cycle) | 0/16 | 4/18 | ns |

Cycle characteristics and responses to treatment are shown in Table 1. The average age of the patients who began DHEA was 41.6±0.6 years. Women in the DHEA group used DHEA for a median value of 16 weeks before their IVF cycle. The cycle cancellation rate was 5 of 21 cycles (21%) pre-DHEA and 1 of 19 (5%) post-DHEA. There was no statistically significant difference in peak estradiol levels between pre- and post-DHEA cycles.

Continuing with the cycle outcomes presented in Table 1, there are improvements in average cell count of day-three embryos and mean embryo grade after DHEA treatment, however the differences are not significant. Mean oocyte numbers, fertilized eggs, day-three embryos, embryos transferred and cumulative embryo scores, all increased significantly after DHEA treatment. In the models adjusted for oocyte number, there was still evidence of increased fertilization rates (1.93 fertilized oocytes, 95% C.I. 0.82-3.04; p<0.005), increased numbers of day-three embryos (1.36 embryos, 95% C.I. 0.34-2.4; p<0.05), and of improved overall embryo score (32.8, 95% C.I. 9.6-56; p<0.01).

FIG. 3 shows paired comparisons of fertilized oocytes (average increase 2.5±0.60; p=0.002) among 12 patients with DHEA treatment cycles of less than about 4 weeks to fertilized oocytes in the same 12 patients after at least about 4 weeks of DHEA treatment. FIG. 4 shows paired comparisons of day 3 embryos (average increase 2.0±0.57; p=0.005) among 12 patients with DHEA treatment cycles of less than about 4 weeks and at least about 4 weeks during IVF cycles. The paired comparisons shows that the mean increase in the number of fertilized oocytes was modest, but significant, (1.42±0.63 increased numbers of fertilized oocytes; p<0.05).

The mean increase in embryo scores was 57±14.7 (p<0.01). The increase in the number of day 3 embryos was 2.0±0.57 (p=0.005) (See FIG. 4) and the increased fertilization quantity was 2.5±0.60 fertilized oocytes per patient (p=0.002) (See FIG. 3).

In addition, two patients achieved ongoing pregnancies while taking DHEA without IVF; one (43 year old) while using DHEA during a stimulated IUI (intrauterine insemination) cycle and a second (37 year old) conceived spontaneously following an unsuccessful IVF cycle. A third patient (40 year old) also conceived spontaneously while preparing for an IVF cycle; however that pregnancy ended in a spontaneous abortion. In all 7 of 45 (16%) patients using DHEA have conceived and 5 of 45 patients (11%) have experienced continuing pregnancies.

EXAMPLE 3

Increased Euploidy Rate

In another study (data not shown), patients were analyzed after four weeks of DHEA treatment. Seven patients had embryos tested by pre-implantation genetic diagnosis (PGD). In three women who had PGD after less than four weeks of DHEA usage and a mean age 41.5±5.1 at the time of starting IVF cycles, the euploidy, or normal chromosome number, rate was 2/30 embryos (6.6%). In six patients who had PGD after more than four weeks of DHEA usage, and a mean age of 43.7±1.3 years at the time of starting IVF cycles, the euploidy rate increased to (8/27; 29.6%), though this trend did not reach statistical significance. There is a mean age difference between patients who underwent IVF after less than four weeks of DHEA usage (mean age 41.5±5.1) and patients who underwent IVF after at least four weeks of DHEA usage (mean age 43.7±1.3).

As women age, there is a substantial decline in euploidy rates in embryos produced. Thus, the increase in euploidy results in older women is dramatic evidence of the effectiveness of DHEA in improving embryo quality because even an identical euploidy result between older women and younger women would indicate effectiveness of DHEA.

EXAMPLE 4

DHEA Substitution Improves Ovarian Function

A case of probable 17, 20-desmolase deficiency, resulting in abnormally low estradiol, DHEA, androstenedione and testosterone levels, is presented in a woman with a clinical history of, initially, unexplained infertility and, later, prematurely aging ovaries.

This patient started attempting conception in 1996, at age 33. After failing to conceive for over one year, she was diagnosed with hypothyroidism and was placed on levoxyl. She, thereafter, remained euthyroid for the whole period described in this case report. She entered fertility treatment at a prominent medical school based program in Chicago, in August of 1997, where, now age 34, she failed three clomiphene citrate cycles. No further treatment took place until a laparoscopy was performed in October of 1999, at a prominent Atlanta-based infertility center (where the couple had relocated to), revealing stage II endometriosis which was laser vaporized. Following surgery, a fourth clomiphene citrate cycle and a first gonadotropin-stimulated cycle failed. Table 2 presents selected key lab data for all ovarian stimulation cycles the patient underwent. A first in vitro fertilization (IVF) cycle was performed, at age 36, in October of 2000.

This cycle resulted in expected oocyte and embryos yields. Three embryos were transferred, resulting in a chemical pregnancy. Three other embryos were cryopreserved. However, because of a persistantly thin endometrium, a number of attempts at transfer were cancelled.

In April of 2001, the patient was, based on an abnormal glucose tolerance test, diagnosed with insulin resistance, and was placed on metformin, 500 mg thrice daily. She had no signs of polycystic ovarian disease: her ovaries did not look polycystic, she was not overweight, had no signs of hirsutism or acne, and androgen, as well as estradiol, levels were in a low normal range (Table 2). In June of 2001 (age 37), a second IVF cycle was initiated. In this cycle the patient demonstrated the first evidence of ovarian resistance to stimulation in that she produced only six oocytes. Only one out of five mature oocyte fertilized, despite the utilization of intracytoplasmic sperm injection (ICSI). The previously cryopreserved embryos were, therefore, thawed and transferred, together with the one fresh embryo from the current cycle. The transfer was unsuccessful.

In August of 2001, the female's FSH level for the first time was abnormally elevated (11.4 mIU/ml), with estradiol levels remaining low-normal. Subsequent FSH levels were 19.1, 9.7 and 9.8 mIU/ml in November and December (twice), respectively, all with low-normal estradiol levels. FSH levels continued to fluctuate in 2002, with levels reported as 11.4 mIU/ml in February, 8.7 in March, 13.6 in June and 19.6 in September, while estradiol levels remained persistently low-normal (Table 2).

A third IVF cycle was started in October of 2002, with a baseline FSH of 11.3 mIUI. Ovarian stimulation, which in the prior two cycles had been given with only recombinant FSH (and antagonists), was now given in a combination of recombinant FSH and hMG at a combined dosage of 300 IU daily. Estradiol levels reached only 890 pg/ml and only 5 oocytes were retrieved. All four mature oocytes fertilized and four embryos were transferred. A twin pregnancy was established by ultrasound and a singleton by heart beat. This pregnancy was, however, miscarried and confirmed as aneuploid with a Trisomy 22.

The fact that this cycle, after the addition of hMG to the stimulation protocol, appeared more successful, led the patient to a search of the medical literature. Like our previously reported patient (Barad and Gleicher, 2005), this patient discovered the case series reported by Casson and associates (Casson et al., 2000). The paper attracted the patient's interest. In follow up, she asked a medical endocrinologist to evaluate her adrenal function. An initial evaluation revealed very low DHEA, DHEA-S, androstenedione and testosterone levels (Table 2). An ACTH-stimulation test was ordered which showed the expected increase in cortisol level, but unchanged, low DHEA, DHEA-S and testosterone levels (Table 3). The patient was advised by her medical endocrinologist that the most likely explanation for such a finding was a 3-beta hydroxysteroid dehydrogenase deficiency. This enzyme defect is, however, associated with an accumulation of DHEA and, therefore, high levels of the hormone. (Speroff et al., 1999a). Such a diagnosis for the patients is, therefore, unlikely. Instead, as FIG. 1 demonstrates, abnormal 17,20-desmolase (P450c17) function would be expected to result in exactly the kind of hormone profile, reported in this patient after ACTH stimulation, characterized by persistently low DHEA, androstenedione, testosterone and estradiol levels, but normal aldosterone and cortisol levels.

In July of 2003, the patient was started on 25 mg daily of micronized DHEA. After five weeks of treatment, DHEA, DHEA-S and androstenedione levels had normalized into mid-ranges. (Even though androstenedione is partially produced through the activity of 17,20-desmolase from 17-hydroxyprogesterone, part is also derived from DHEA through the activity of 3-beta hydroxysteroid dehydrogenase [Speroff et al., 1999a]. The normalization of andostenedione, after DHEA administration, therefore, also speaks for an underlying 17,20-desmolase defect, and not a 3-beta hydroxysteroid dehydrogenase deficiency.) In the third and fourth month, following the start of DHEA supplementation, the patient ovulated spontaneously with estradiol levels of 268 and 223 pg/ml (Table 2), respectively, measured on the day of LH surge.

On Jan. 28, 2004 (age 39), and after DHEA therapy of approximately six months, a fourth IVF cycle was initiated. Her baseline FSH level in that cycle was 9.6 mIU/ml, estradiol 56 pg/ml. Stimulation took place with 300 IU of recombinant FSH (without hMG) and with an agonist flare protocol. Estradiol levels reached a peak of 1764 pg/ml, 8 oocytes were retrieved, six out of seven mature oocytes fertilized and six embryos were transferred. A triplet pregnancy was established with heart beats. Two, out of the three fetuses lost heart beat spontaneously, and the patient delivered by cesarean section, at term, a healthy singleton male infant.

At surgery, her ovaries were closely inspected and described as "old" and "small", with the left one being described as "almost dead." DHEA and DHEA-S levels at six months of pregnancy were reported at "record lows." DHEA-S, six weeks post-delivery, was still very low (Table 2). At time of this report, the male offspring is nine months old and the mother has been re-started on DHEA in an attempt at another pregnancy.

DHEA substitution resulted in apparently normal peripheral DHEA levels, spontaneous ovulation and normal estradiol production by the ovaries. An in vitro fertilization (IVF) cycle, after approximately six months of DHEA substitution, showed, in comparison to a pre-DHEA IVF cycle, improved peak estradiol levels, increased oocyte and embryo numbers and resulted, at age 39, after 6 years of infertility therapy, in a triplet pregnancy and a normal singleton delivery.

Low DHEA levels appear associated with female infertility and ovarian aging. DHEA substitution normalizes peripheral DHEA levels and appears to improve ovarian response parameters to stimulation.

The reported patient exhibited some of the classical signs of prematurely aging ovaries (Nikolaou and Templeton, 2003; Gleicher N, 2004) which include ovarian resistance to stimulation, poor egg and embryo quality and prematurely elevated FSH levels.

We have previously suggested that the decrease in DHEA levels, with advancing female age, may be an inherent part of the ovarian aging process and may, at least in part, and on a temporary basis, be reversed by external DHEA substitution (Barad and Gleicher, 2005, 2005a). This case demonstrates that low DHEA levels are, indeed, associated with all the classical signs of both prematurely and normally aging ovaries. While association does not necessarily suggest causation, the observed sequence of events in this patient supports the notion that low DHEA levels adversely affect ovarian function.

The patient was initially thought to have largely unexplained infertility. Approximately 10 percent of the female population is believed to suffer from premature aging ovaries and this diagnosis is, indeed, often mistaken for unexplained infertility (Nikolaou and Templeton, 2003, Gleicher N, 2005). She later developed quite obvious signs of prematurely aging ovaries and, finally, even showed elevated FSH levels. In the time sequence, in which all of these observations were made, the patient followed the classical parallel, premature aging curve we, and others, have previously described (Nikolaou and Templeton, 2003; Gleicher N, 2005).

Once substituted with oral DHEA, a reversal of many findings characteristic of the aging ovary, was noted. First, the patient's DHEA and DHEA-S levels normalized. In subsequent natural cycles an apparently normal spontaneous follicular response was observed, with normal ovulatory estradiol levels in a patient with persistently low estradiol levels before DHEA treatment (Table 2). The response to ovarian stimulation improved, quantitatively and qualitatively, as the patient improved peak estradiol levels, oocyte and embryo numbers and, as the successful pregnancy may suggest, also embryo quality.

A case report can, quite obviously, not be seen as confirmation for all of these observations. Moreover, one cannot preclude that other factors contributed. For example, the ovarian stimulation protocol had switched from an antagonist to an agonist flare protocol. Yet, our previously reported data quite convincingly demonstrates that DHEA supplementation in women with aging ovaries, indeed, to a statistical degree, improves oocyte yield and egg as well as embryo quality (Barad and Gleicher, 2005a). Our data also suggest that DHEA may improve pregnancy rates and reduce aneuploidy rates in embryos from older women, though the latter two outcome modifications are not yet statistically robust. Finally, our data have demonstrated that a maximal effect of DHEA is achieved after at least about four consecutive months of use (Barad and Gleicher, 2005a). This patient was on DHEA treatment for approximately six months before she conceived the pregnancy that led to her first live birth.

This case is unusually well documented in its DHEA deficiency and in its most likely cause. We are considering the diagnosis of 17,20-desmolase deficiency as very likely, though not absolutely proven, since only a tissue diagnosis, or adrenal outflow cannulation, can offer absolute proof of an adrenal enzyme defect. Neither procedure has, so far, been performed in this case. The reported adrenal response to ACTH stimulation (Table 2) allows, however, no other explanation (FIG. 1).

TABLE 2

Relevant laboratory results

| Date | TEST | RESULT (Normal values)* | COMMENTS |
| --- | --- | --- | --- |
| August 1997 | TSH | 7.8 mIU/l (0.4-5.5) | Diagnosis of hypothyroidism |
| May 1999 | FSH | 4.0 mIU/ml | |
| April 2001 | Glucose tolerance test | Elevated ½ hour insulin levels Normal Glucose levels | Diagnosis of insulin resistance |
| June 2001 | FSH | 7.7 mIU/ml | |
| | Estradiol | 33 pg/ml | |
| August 2001 | Testosterone free/weakly bound | 2 ng/dl (3-29) | |

TABLE 2-continued

Relevant laboratory results

| Date | TEST | RESULT (Normal values)* | COMMENTS |
|---|---|---|---|
| | free only | 1 pg/ml (1-21) | |
| | total | 13 ng/dl (15-70) | |
| | DHEA-S | 96 mcg/dl (12-379) | |
| | Total Cortisol | 14.2 mcg/ml (4-22) | |
| | FSH | 11.4 mIU/ml | Diagnosis of prem. ov. aging |
| | Estradiol | 45 pg/ml | |
| October 2001 | Estradiol periovulatory | 119 pg/ml | |
| November 2001 | Testosterone total | 23 ng/ml (14-76) | |
| | Androstenedione | 98 ng/ml (65-270) | |
| | Ovarian antibodies | negative | |
| | FSH | 19.1 mIU/ml | |
| | Estradiol | 23 pg/ml | |
| December 2001 | FSH | 9.7 mIU/ml | |
| | Estradiol | 27 pg/ml | |
| February 2002 | Testosterone total | <20 ng/dl (20-76) | |
| | Androstenedione | 76 ng/dl (65-270) | |
| | FSH | 11.4 mIU/ml | |
| | Estradiol | 28 pg · ml | |
| March 2002 | Testosterone total | 16 ng/dl (15-70) | |
| | FSH | 8.7 mIU/ml | |
| | Estradiol | 29 pg/ml | |
| May 2002 | FSH | 13.6 mIU/ml | |
| | Estradiol | 30 pg/ml | |
| | periovulatory | 139 pg/ml | |
| June 2002 | periovulatory | 50 pg/ml | |
| September 2002 | Testosterone total | 15 ng · dl (15-70) | |
| | free | 1.6 pg/ml (1-8.5) | |
| | % free | 0.0107 (0.5-1.8) | |
| | Estradiol periovulatory | 136 pg/ml | |
| October 2002 | FSH | 11.3 mIUI/ml | |
| | Estradiol | 43 pg/ml | |
| February 2003 | FSH | 13.6 mIU/ml | |
| | Estradiol | 33 pg/ml | |
| March 2003 | FSH | 8.9 mIU/ml | |
| | Estradiol | 67 pg/ml | |
| May 2003 | Anti-adrenal antibodies | negative | |
| | Estradiol periovulatory | 139 pg/ml | |
| | DHEA | 132 ng/dl (130-980) | |
| | DHEA-S | 79 mcg/dl (52-400) | |
| | Testosterone total | 34 ng/dl (20-76) | |
| | free | 3 pg/ml (1-21) | |
| July 2003 | | DHEA TREATMENT START | |
| | DHEA | 296 ng/dl (130-980) | |
| | DHEA-S | 366 mcg/dl (52-400) | |
| | Androstenedione | 121 ng/dl (65-270 | |
| September 2003 | Estradiol periovulatory | 268 pg/ml | |
| October 2003 | FSH | 14.7 mIUI/ml | |
| | Estradiol | 44 pg/ml | |
| | priovulatory | 224 pg/ml | |
| November 2003 | FSH | 17 mIU/ml | |
| | Estradiol | 38 pg/ml | |
| December 2003 | DHEA | 278 ng/ml (130-980) | |
| | DHEA-S | 270 mcg/dl (52-400) | |
| | Testosterone total | 25 ng/ml (20-76) | |
| | free and weekly bound | 4 ng/dl (3-29) | |
| | free | 2 pg/ml (1-21) | |
| January 2004 | FSH | 18 mIU/ml | |
| | FSH | 9.6 mIU/ml | 4th IVF |
| | Estradiol | 56 pg/ml | CYCLE START |
| August 2004 | MID_PREGNANCY DHEA | 74 ng/dl (135-810) | |
| | DHEA-S | 27 mcg/dl (**) | |
| October 2004 | | | DELIVERY |
| December 2004 | DHEA-S | 52 mcg/dl (44-352) | |

*Laboratory tests were performed at varying laboratories
(**) No pregnancy levels available from laboratory

TABLE 3

| | ACTH stimulation test | | |
|---|---|---|---|
| HORMONE | BASELINE | +30 MINUTES | +60 MINUTES |
| DHEA-S (mcg/ml) | 87 | 88 | 83 |
| Cortisol total (mcg/dl) | 15 | 26 | 27 |
| Testosterone total (ng/dl) | 28 | 32 | 33 |
| free and weakly bound | 5 | 5 | 5 |
| free | 3 | 3 | 3 |

This case is also remarkable in that it includes evidence of ovarian, thyroid, pancreatic and adrenal dysfunction in one patient. Such a combination of glandular involvements has been reported in the autoimmune polyglandular syndrome(s), characterized by combined end-organ involvements in an autoimmune assault of thyroid, parathyroid, adrenal, pancreas, ovary and, at times, other organs. It appears that at least some of these cases are inherited in Mendelian fashion as an autosomal recessive disorder (Consortium, 1997). End-organ function may be vulnerable to autoantibody attacks with various cross-reactivities. For example, women diagnosed with both adrenal and ovarian insufficiency have been shown to demonstrate antibody activity against P450scc, the adrenal enzyme essential to steroidogenesis (Winqvist et al., 1995). It has been suggested that any one of the vital enzymes, involved in steroidogenesis, may be vulnerable to autoimmune inactivation. (Speroff et al., 1999b).

Considering this patient's hypothyroidism, insulin resistance, premature ovarian aging process and, quite obviously, selective adrenal insufficiency, she deserves close observation in regards to the possible appearance of other characteristic features of the autoimmune polyglandular syndrome(s). It is also noteworthy that she reports a family history in support of a potential genetic predisposition: Her brother's son has been diagnosed with congenital adrenal hyperplasia, which can be caused by 21-hydroxilase (P450c21)-, 11 beta hydroxylase (P450c11-beta)- or 3-beta hydroxysterod dehydrogenase deficiencies (Speroff et al., 1999a). And her father required testosterone substitution to initiate puberty.

This case report also presents further evidence for DHEA deficiency as a cause of female infertility and as a possible causative agent in the aging processes of the ovary. It also presents further confirmation of the value of DHEA substitution whenever the suspicion exists that ovaries may be lacking of DHEA substrate. Finally, this case report raises the important question what the incidence of adrenal 17,20-desmolase (P450c17) deficiency is in women with prematurely aging ovaries. Why ovaries age prematurely is, in principle, unknown. Since the process is familial (Nikolaou and Templeton, 2003), it is reasonable to assume that, like other adrenal enzymatic defects, 17,20-desmolase deficiency, may occur in either a sporadic or an inherited form. As both forms will result in abnormally low DHEA levels, both may then, indeed, lead to phenotypical expression as premature ovarian aging.

While the foregoing written description of the invention enables one of ordinary skill to make and use what is considered presently to be the best mode thereof, those of ordinary skill will understand and appreciate the existence of variations, combinations, and equivalents of the specific exemplary embodiments thereof. The invention is therefore to be limited not by the exemplary embodiments herein, but by all embodiments within the scope and spirit of the appended claims.

What is claimed is:

1. A method of increasing human female fertility through in vitro fertilization by improving quality of a human embryo as measured by an improved human embryo score, said method comprising:

administering about 75 mg per day of dehydroepiandrosterone to a human female for at least or equal to four consecutive months without concurrent administration of gonadotropin, wherein said human female is a premenopausal human female with diminished ovarian reserve;

harvesting a plurality of oocytes from said human female; and fertilizing said plurality of oocytes and forming at least one human embryo having an improved human embryo score, said at least one human embryo comprising a plurality of cells and cytoplasm;

wherein said improved human embryo score is based on factors including uniformity of said cells, amount of fragmentation of said cells, and color and consistency of said cytoplasm.

2. A method according to claim 1 further comprising inducing ovulation in said human female prior to said harvesting said plurality of oocytes.

3. A method according to claim 1 wherein said at least one human embryo comprises a plurality of human embryos, and said improved human embryo score increases a cumulative embryo score, wherein said cumulative embryo score is a product of multiplying said human embryo score by said plurality of human embryos by a number of cells in each said plurality of human embryos, and further wherein said cumulative embryo score is at least or about 90.

4. A method according to claim 1 wherein said human female is over 40 years in age.

* * * * *